United States Patent [19]
Landegren et al.

[11] Patent Number: 5,952,201
[45] Date of Patent: Sep. 14, 1999

[54] METHOD OF PREPARING OLIGONUCLEOTIDE PROBES OR PRIMERS, VECTOR THEREFOR AND USE THEREOF

[76] Inventors: Ulf Landegren, Eksoppsvägen 16, S-756 46 Uppsala, Sweden; Mats Sundvall, Salagatan 28 B, S-753 30 Uppsala, Sweden

[21] Appl. No.: 08/836,222

[22] PCT Filed: Nov. 7, 1995

[86] PCT No.: PCT/SE95/01319

§ 371 Date: May 7, 1997

§ 102(e) Date: May 7, 1997

[87] PCT Pub. No.: WO96/14406

PCT Pub. Date: May 17, 1996

[30] Foreign Application Priority Data

Nov. 7, 1994 [SE] Sweden .................................. 9403805

[51] Int. Cl.$^6$ .............................. C12P 19/34; C12N 15/10
[52] U.S. Cl. .................... 435/91.2; 435/91.52; 435/320.1
[58] Field of Search .............................. 435/6, 91.1, 91.2, 435/91.21, 91.4, 91.41, 91.42, 91.5, 91.52, 91.53, 172.1, 172.3, 320.1, 476; 935/22; 536/24.2, 24.3, 24.33

[56] References Cited

U.S. PATENT DOCUMENTS

| | | | |
|---|---|---|---|
| 4,808,519 | 2/1989 | Hartley et al. ............................... | 435/6 |
| 4,883,750 | 11/1989 | Whiteley et al. ............................ | 435/6 |
| 4,988,617 | 1/1991 | Landegren et al. .......................... | 435/6 |
| 5,242,794 | 9/1993 | Whiteley et al. ............................ | 435/6 |
| 5,426,180 | 6/1995 | Kool ........................................ | 536/25.3 |
| 5,516,663 | 5/1996 | Backman et al. ....................... | 435/91.2 |

FOREIGN PATENT DOCUMENTS

| | | |
|---|---|---|
| 0 185 494 A2 | 6/1986 | European Pat. Off. . |
| 0 320 308 A2 | 6/1989 | European Pat. Off. . |
| 0 324 616 A2 | 7/1989 | European Pat. Off. . |
| 0 336 731 A2 | 10/1989 | European Pat. Off. . |
| 0 473 155 A2 | 3/1992 | European Pat. Off. . |
| 4-262799 | 9/1992 | Japan . |
| 4-304900 | 10/1992 | Japan . |
| 90/01548 | 2/1990 | WIPO . |
| 94/11529 | 5/1994 | WIPO . |
| 95/22623 | 8/1995 | WIPO . |

OTHER PUBLICATIONS

New England Biolabs Catalog, pp. 22, 106, 107, 148, and 149, 1992.

Boyd, A.C., Charles, I.G., Keyte, J.W., and Brammar, W.J., "Isolation and computer–aided characterization of MmeI, a Type II restriction endonuclease from *Methylophilus methotrophus,*" *Nucleic Acids Research,* 14(13):5255–5274 (1986).

Gayle III, R.B., Auger, E.A., Gough, G.R., Gilham, P.T., and Bennett, G.N., "Formation of *Mbo*II vectors and cassettes using asymmetric MboII linkers," *Gene,* 54(2&3):221–228 (1987).

Janulaitis, A., Bitinaité, J., and Jaskeleviciené, B., "A new sequence–specific endonuclease from *Gluconobacter suboxydans,*" *FEBS Letters,* 151(2):243–247 (1983).

Klimašauskas, S., Timinskas, A., Menkevicius, S., Butkienè, D., Butkus, V., and Janulaitis, A., "Sequence motifs characteristic of DNA," *Nucleic Acids Research,* 17(23):9823–9832 (1989).

Nilsson, M., Malmgren, H., Samiotaki, M., Kwiatkowski, M., Chowdhary, B.P., and Landegren, U., "Padlock Probes: Circularizing Oligonucleotides for Localized DNA Detection," *Science,* 265:2085–2088 (Sep., 1994).

Petrušyté, J., Menkevičius, S., Klimašauskas, S., Butkus, V., and Janulaitis, A., "Restriction endonuclease of a new type," *Gene,* 74:89–91 (1988).

Derwent World Patent Index (Dialog file 351) English–language Abstract for JP 4–262799, Dialog accession No. 009233973.

English–language Translation of JP 4–304900.

Derwent World Patents Index (Dialog file 351, English–language Abstract for JP 4–304900, Dialog accession No. 009282380.

Fischer, S. et al., "Integrated Mapping of YAC and Cosmid Contigs of Human Chromosome 13," in: Abstracts of Papers Presented at the 1994 Meeting on Genome Mapping and Sequencing, May 11–15, 1994, Cold Spring Harbor Laboratory, Cold Spring Harbor, NY, Cold Spring Harbor Laboratory Meetings Department, pub., p. 67 (May 1994).

Jäschke, A. et al., "Automated Incorporation of Polyethylene Glycol into Synthetic Oligonucleotides," *Tetrahedron Letters* 34(2):301–304 (Jan. 1993).

Nilsson, M. et al., "Padlock–Probes for *in situ* Detection of Gene Sequences," summary of poster presented at the 1994 Meeting on Genome Sequencing and Mapping, May 11–15, 1994, Cold Spring Harbor Laboratory, Cold Spring Harbor, NY, total of 3 pages (May 1994).

Nilsson, M. et al., "Padlock–Probes for in situ Detection of Gene Sequences," in: Abstracts of Papers Presented at the 1994 Meeting on Genome Mapping and Sequencing, May 11–15, 1994, Cold Spring Harbor Laboratory, Cold Spring Harbor, NY, Cold Spring Harbor Laboratory Meetings Department, pub., p. 190 (May 1994).

(List continued on next page.)

*Primary Examiner*—Nancy Degen
*Assistant Examiner*—Thomas G. Larson
*Attorney, Agent, or Firm*—Sterne, Kessler, Goldstein & Fox P.L.L.C.

[57] ABSTRACT

A method of preparing a nucleic acid sequence capable of hybridizing to a target DNA sequence without requiring knowledge of this DNA sequence comprises the steps of ligating or otherwise linking a DNA fragment related to the target DNA sequence to a nucleotide sequence containing the recognition motif of an asymmetrically cleaving restriction enzyme, and subjecting the construct to the restriction enzyme to thereby cleave the construct within the target-related DNA fragment part thereof. A vector therefor comprises a site for insertion of the target-related DNA fragment, and a recognition sequence for an asymmetrically cleaving restriction enzyme or enzymes on one or both sides of said insertion site.

30 Claims, 4 Drawing Sheets

OTHER PUBLICATIONS

Nilsson, M. et al., "Padlock Probes: Circularizing Oligonucleotides for Localized DNA Detection," *Science* 265:2085–2088 (Sep. 1994).

Sund, C. et al., "Construction of Europium ($Eu^{3+}$)–labelled Oligo DNA Hybridization Probes," *Nucleosides & Nucleotides* 7(5&6):655–659 (1988).

Zhang, P. et al., "A Statistical Distance Approach for the Orientation and Ordering of Multiple Non–overlapping Contigs," in: Abstracts of Papers Presented at the 1994 Meeting on Genome Mapping and Sequencing, May 11–15, 1994, Cold Spring Harbor Laboratory, Cold Spring Harbor, NY, Cold Spring Harbor Laboratory Meetings Department, pub., p. 290 (May 1994).

METHOD OF PREPARING OLIGONUCLEOTIDE PROBES OR PRIMERS, VECTOR THEREFOR AND USE THEREOF

This is a national phase filing of PCT International Application PCT/SE95/01319, filed Nov. 07, 1995.

FIELD OF THE INVENTION

The present invention relates to the preparation of nucleic acid probes and primers as well as vectors therefor.

BACKGROUND OF THE INVENTION

The polymerase chain reaction, or PCR, provides a highly efficient method of isolating a desired gene sequence(s) from different DNA samples. One general requirement is that sequence information is available from both ends of the fragment to be amplified in order to synthesize specific amplification primers. The expense of sequencing DNA and then chemically synthesizing primers still limits the scope of many applications. In many investigations it would therefore be most helpful if the steps of DNA sequencing and oligonucleotide synthesis could be avoided entirely before genomic fragments are amplified by PCR. This is true for instance for the large programs designed to analyze the degree of polymorphism of specific DNA segments in individuals in a population, in order to identify polymorphic markers in the human or other genomes. Such genetic markers are required for mapping genetic disease and to establish or extend genetic linkage maps for a variety of organisms.

One approach which partially overcomes the above problem is the use of relatively nonspecific amplification with a limited set of primers under nonstringent conditions, so called RAPD markers. These markers serve as a means to establish relatively random polymorphic markers, analyzable by PCR without requiring DNA sequencing and chemical oligonucleotide synthesis of specific primers.

SUMMARY OF THE INVENTION

The present invention provides a different strategy to overcome the deficiences of the prior art methods and permits enzymatic synthesis of specific amplification primers, ligation probes or other probes of known structure but partially unknown sequence without access to clone specific DNA sequence information.

In one aspect, the invention provides a vector for the preparation of a nucleic acid sequence of known structure but partially unknown sequence, capable of hybridizing to a target DNA sequence without requiring knowledge of this DNA sequence, which vector comprises a site for the insertion of a DNA fragment related to the target DNA sequence, and a recognition sequence for an asymmetrically cleaving restriction enzyme or enzymes on one or both sides of said insertion site.

In another aspect, the invention provides a method of preparing a nucleic acid sequence of known structure but partially unknown sequence, capable of hybridizing to a target DNA sequence without requiring knowledge of this DNA sequence, which method comprises the steps of ligating or otherwise linking a DNA fragment related to the target sequence to a nucleotide sequence containing the recognition motif of an asymmetrically cleaving restriction enzyme, and subjecting the construct to the restriction enzyme to cleave the construct within the DNA fragment part thereof.

In still another aspect, the invention provides a method for amplifying a DNA fragment without requiring knowledge of the DNA sequence of the fragment by using enzyme-synthesized primers prepared according the above aspect of the invention.

In yet another aspect, the invention provides a method for constructing probes for target-dependent ligation reactions.

Other aspects and advantages of the present invention will be apparent upon consideration of the following detailed description thereof which includes an illustrative example of the practice of the invention.

The invention will be described in more detail below with reference to the accompanying drawings.

DETAILED DESCRIPTION OF THE INVENTION

A restriction endonuclease, or restriction enzyme, is an enzyme capable of recognizing a specific DNA sequence (usually four to eight nucleotides in sequence) and cleaving the DNA, thereby creating double-stranded breaks. The restriction enzymes are grouped into four classes, type I, II, III and IV, on the basis of their subunit structure, cofactor requirements, substrate specificity and several other features. Type I enzymes cleave the substrate DNA almost at random at a great distance from the recognition site. Type II enzymes, exemplified by EcoRI, cleave within the recognition site or a few nucleotides away. Both type III and type IV enzymes cleave the target DNA sequence some considerable distance away from the recognition site and they also have in common the property of never cleaving the DNA to completion. Type IV enzymes differ from the type III enzymes in that they, similar to the type II restriction enzymes, are not dependent upon ATP. The type III and type IV restriction enzymes are commonly called asymmetrically cleaving enzymes. Exemplary of type IV restriction enzymes are GsuI (Janulaitis et al., Nucl. Acid Res. 1989; 17(14):1989), with the recognition motif 5'CTGGAG3' and cleaving 16 bases downstream of this motif; Eco57I, with the recognition sequence 5'CTGGTG3' and cleaving 16 bases downstream of this motif; MmeI (Boyd et al., Nucl. Acid Res. 1986; 17(14):5255–5274, with a 6-base recognition motif, and which cleaves the target DNA 22 bases downstream of this sequence. Restriction enzyme BpmI (available from New England Biolabs, U.S.A.) has the same recognition sequence and cleaves in the same way as GsuI above. There are also type III or IV enzymes cleaving the target DNA even farther from the recognition sequence. Examples of such enzymes include Eco15 and HinP15I cleaving 25 or 26 bases downstream of the recognition sequence.

According to the present invention, the property of type III or IV restriction enzymes to cleave asymmetrically, i.e. to cleave a DNA substrate at a distance from the recognition sequence, is utilized to prepare probes or primers of a defined size capable of hybridizing to a target DNA sequence without a requirement to know this DNA sequence.

In one embodiment of the invention, amplification primers are prepared which may then be used, optionally in combination with a standard vector sequence-derived oligonucleotide, for amplification to large copy numbers, starting from a genomic DNA sample.

Thus, defined size amplification primers may be produced enzymatically through digestion inside the cloned fragments in amplification products by locating a recognition sequence for an asymmetrically cleaving restriction enzyme on both sides of the cloning site. The digestion is independent of the DNA sequence of the cloned fragment, and the cleavage products consisting of the original amplification primers having linked thereto a respective part of the cloned DNA fragment may be used to amplify sequences corresponding to the cloned DNA fragment from other DNA samples. Such a procedure for producing amplification primers will now be described in more detail.

Figure 1A:
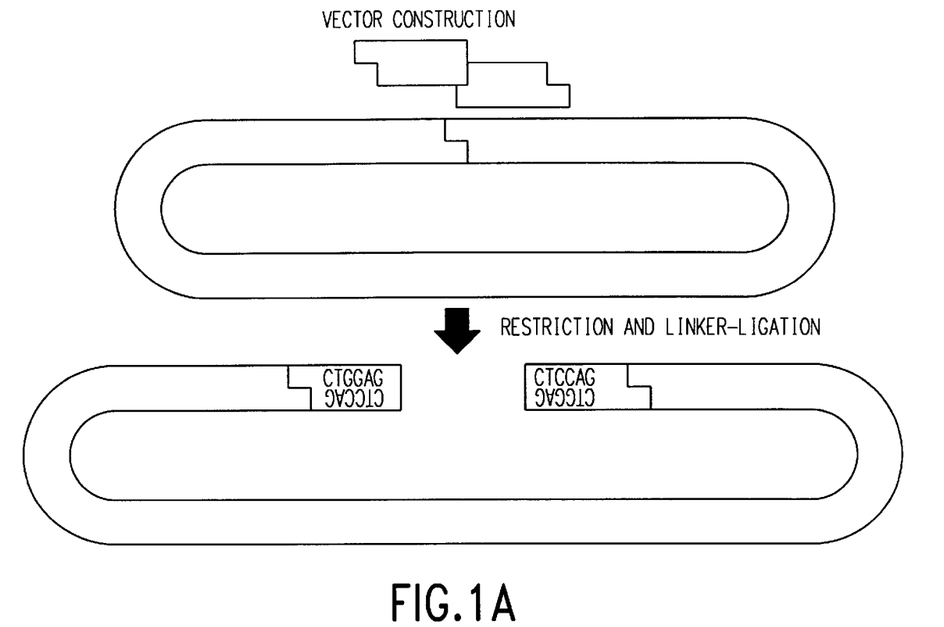
FIGS. 1A and 1B are a schematic representation, in the form of four parts A–D, of a strategy to derive amplification primers enzymatically. Part A shows the construction of a specialized cloning vector, part B shows the cloning of an AluI fragment into the vector, part C shows enzymatic synthesis of amplification primers, and part D shows amplification of sequences corresponding to those cloned in the vector using primers derived from the amplified insert of the clone. The recognition sequences of the restriction enzymes GsuI and AluI are highlighted in the figures.

With reference to FIG. 1A, part A, a plasmid vector is cleaved at a desired site, and an oligonucleotide duplex, or linker, containing the recognition site for an asymmetrically cleaving restriction enzyme, in the figure by way of example the recognition motif for GsuI, is ligated to each vector fragment end. Both linkers lack 5'-phosphate groups to prevent them from ligating to themselves. Ligation of linkers to the restriction fragment ends does not recreate the restriction site, so that over time more and more restriction ends are modified with linker dimers. The vector produced is then isolated, e.g. by gel purification, from remaining circular vector molecules and used for molecular cloning of DNA fragments. This is schematically illustrated in FIG. 1A, part B which shows the construction of a recombinant molecule by ligating a blunt end AluI-cleaved DNA-fragment into the vector.

In order to produce amplification primers, individual clones are amplified using a single primer corresponding to one of the linker oligonucleotides and with the 5'-end protected against λ exonuclease digestion, e.g. by a biotin residue at the 5' end. The resulting amplification products consist in the cloned AluI-fragment surrounded by vector-derived sequences representing the oligonucleotide dimer ligated to the vector as described above. With reference to part C of FIG. 1A, the 6-base motif, 5'CTGGAG3', immediately flanking the insert cloned into the vector, represents the recognition sequence for the restriction enzyme GsuI. As mentioned above, this enzyme cleaves the DNA molecule 16 bases downstream of this motif, inside the fragment cloned into the vector. After digesting the amplification products with this enzyme, the fragments obtained are separated by gel electrophoresis. Thereby the fragments derived from both ends of the amplification product may be quantitated and isolated from remaining undigested or partially digested molecules. Finally, any DNA strands that have 5' phosphate groups are removed by digestion with the enzyme λ exonuclease, whereas the extension products containing 5' biotin are insensitive to the exonuclease over a wide range of nuclease concentrations. In this manner, pairs of single-stranded amplification primers are obtained, which consist of a 5' end part, derived from the linker sequence that was added to the cloning vector by linker ligation, and a 3' end part, derived from ends of the inserts cloned into the vector. In the illustrated case (FIG. 1A, part C) there is located immediately upstream of these 16 bases in the primers a dinucleotide, AG, representing the last two positions in the recognition sequence for the enzyme GsuI. These positions are also known to be present in the genomic DNA from which the cloned fragment was derived since these fragments were derived by digestion with the blunt end generating restriction enzyme AluI (FIG. 1A, part C). Each one of the enzyme-synthesized primers therefore has a number (here 18) of bases (the 3' end bases plus two of the 5' end bases) that are complementary to the genomic sequence at each side of the cloned fragment, and a number of bases derived from the vector.

Figure 1B:
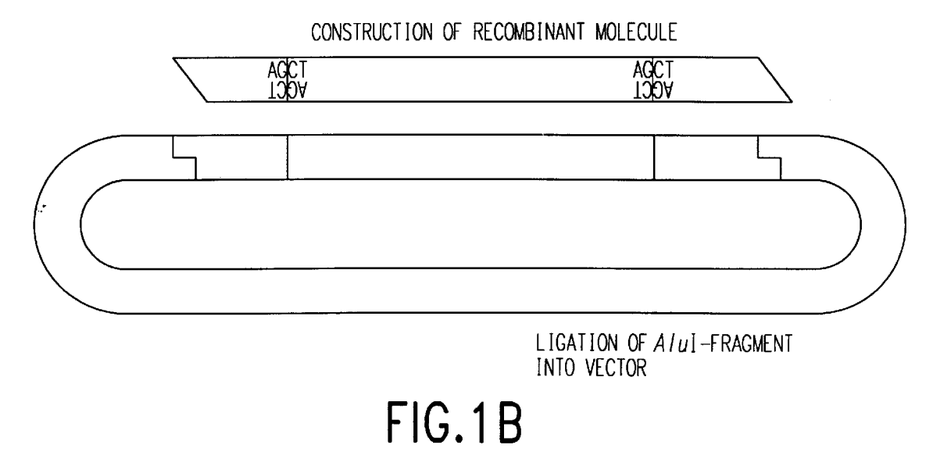
Figure 1C:
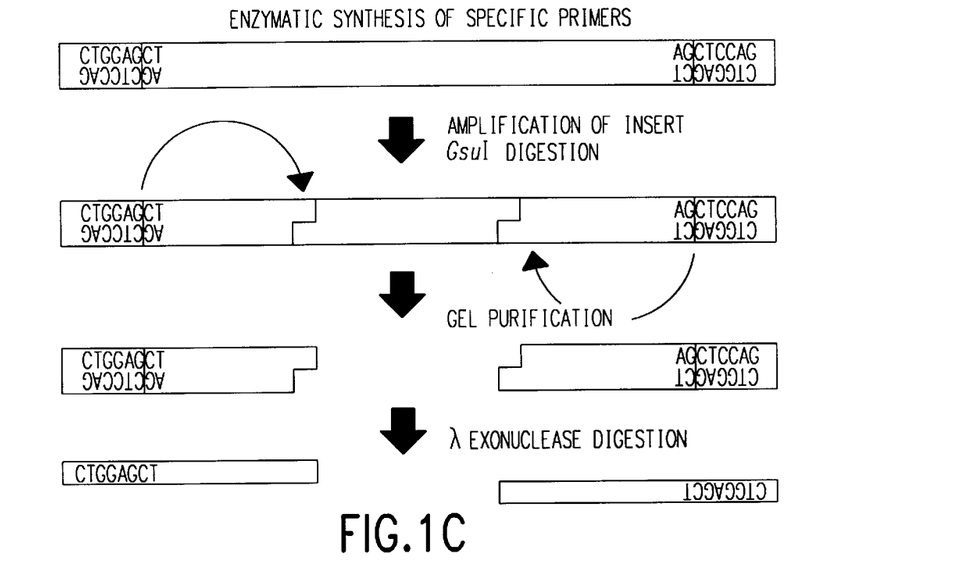
Figure 1D:
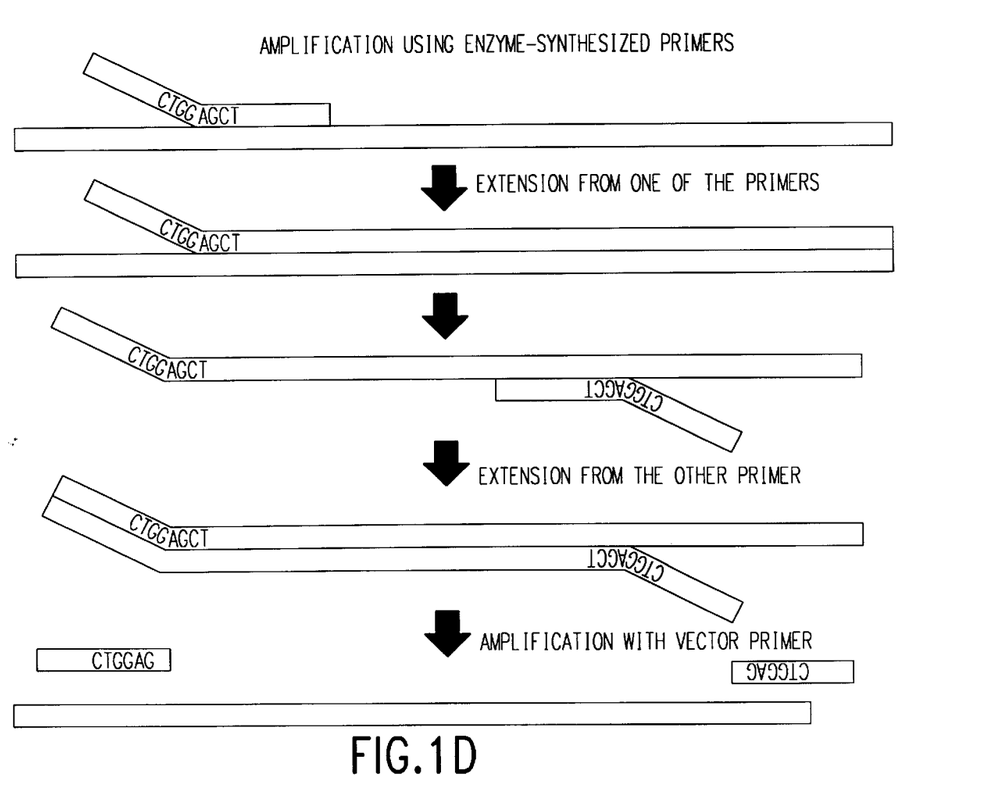

The above enzymatically synthesized primers may be used for PCR amplification of a fragment obtained by AluI digestion of chromosomal DNA as schematically illustrated in FIG. 1B, part D. First, the primers are used in a number of, say 5, amplification cycles, when necessary using a long annealing time to compensate for relatively low concentration of enzyme-synthesized primers. In these first cycles, the desired DNA fragments are obtained, flanked at either end by the vector sequence. It is then no longer necessary to use the enzymatically synthesized primers, but the further amplification of the fragments to large numbers may conveniently be performed with the "standard" vector-derived primer, i.e one of the linker primers or a variant thereof.

In a variant of the above procedure, a cloning vector is prepared which contains the two recognition sites for the asymmetrically cleaving enzyme immediately adjacent each other but in opposite orientations and together containing the recognition site for a bluntly cleaving restriction enzyme, such that the enzyme may cleave right between the two sites. This permits the cloning vector containing the two recognition sites for the asymmetrically cleaving enzyme to be amplified prior to blunt cleavage between the sites, phosphatase treatment to prevent self-ligation of the free vector ends, and insertion and ligation of the target DNA sequence to be subsequently cleaved by the asymmetrically cleaving enzyme. As an example may be mentioned two juxtaposed but opposed GsuI (or BpmI) sites which can be bluntly cleaved between them by the restriction enzyme Ecl136II (New England Biolabs, U.S.A.)

As appears from the above, the steps of the present procedure are simple and may easily be performed for a large number of fragments in parallel, permitting the development of large sets of genetic markers. If desired, successful markers may be sequenced and converted to regular chemically synthesized PCR-based primers, but it is also possible to continue using enzyme-synthesized primers.

Enzymatically synthesized amplification primers, constructed as described above, can also provide highly specific and sensitive detection reagents. Thus, in another embodiment of the invention, amplification primers suitable to detect individual organisms in complex mixtures by PCR may be obtained by restriction digesting DNA preparations, cloning the fragments into the specialized vector described above, and isolating individual clones in order to generate a desired number of pairs of amplification primers. These amplification primers may thus be developed and tested without any requirement for access to DNA samples from isolated organisms or for DNA sequence information from these.

In order to avoid the risk of contamination by another fragment, amplifiable with the same standard primer, precautions such as the inclusion of a ribose in the 3' position of the standard primer, rendering amplification products cleavable by alkali, may be contemplated.

It is readily seen that the same DNA fragment may be cloned into two different vectors with different linkers, or "standard primers", permitting so-called nested PCR to be performed. This is possible by using different flanking sites for enzymes that cleave at variable distances internal to the cloned fragment. In nested PCR, a number of cycles are conducted with a first set of primers, whereupon a number of cycles are run with a second set of primers hybridizing internally of the first primer set. This increases the efficiency and selectivity of the PCR process.

As is readily realized, it is essential in the preparation of the synthesized primers to isolate the desired end fragments obtained after cleavage with the asymmetrically cleaving enzyme from any remaining partially digested or undigested amplification products as incomplete digestion products may give rise to false positives in the subsequent amplification, when using the enzymatically derived primers. In the preparation procedure described above, gel electrophoresis is used to isolate the desired fragments. However, preparative gel electrophoresis is relatively cumbersome and may also fail to adequately resolve end fragments and incomplete digestion products. An alternative means of removing middle piece-containing fragments away from the desired end fragments is described below.

Despite the fact that the middle segments are of unknown sequence composition, end fragments may be efficiently isolated by amplifying the cloned fragments in two separate reactions as follows:

In each of the two amplifications of the cloned inserts, one or the other amplification primer is biotinylated, permitting the amplified molecules to be isolated on a solid support, such as streptavidin-coated combs, e.g. of the type described in WO 94/11529, or paramagnetic particles. Other means of immobilization including DNA ligation may also be used. After adequate washes, one or the other of the end fragments are released from the rest of the amplified molecules by selectively digesting the asymmetric restriction enzyme site located at the end remote from the support. This selective digestion may be achieved by using vectors with recognition sequences for two different asymmetric restriction enzyme sites, e.g. type IV enzymes, on each side of the cloned inserts and cleaving the immobilized, amplified molecules in two separate reactions. Examples of such pairs of type IV restriction enzymes are GsuI and Eco57I.

Alternatively, vectors with a single restriction site on both sides of the insert may be used if the biotinylated amplification primers are designed such that they are mismatched to the vector in e.g. positions 5 and 6 in from the 3' end of the primer, corresponding to the first 2 bases of the 6 base recognition sequence of a type IV restriction enzyme. Other sequence alterations are, of course, also possible, preserving the ability of the primers to amplify the cloned fragment but destroying the recognition sequence for one or the other of the sites. In this strategy, the two amplification products may be pooled before immobilization on the supports and restriction cleavage. After cleavage, released fragments are treated with λ-exonuclease to obtain single stranded probes, and may then be directly used as enzymatic amplification primers.

The enzymatic primer synthesis approach of the invention may also be used for producing circularizable probes. The preparation and use of circularizable probes (so-called "padlock" probes) have been described by Landegren et al., Science 265, 2085–2088 (1994). Such probes consist of two target-complementary segments, connected by a linker sequence. Upon recognition of a specific nucleic acid molecule, the ends of the probe are joined through the action of a ligase, creating circular DNA molecules catenated to the target sequence. These probes provide highly specific detection with minimal background.

In accordance with another embodiment of the invention, such a circularizable probe may be prepared by cloning a DNA sequence into a specially designed vector, and the vector may then be used as a circularizable probe without the use of DNA sequence information from the cloned fragment, or the use of specific oligonucleotides. A large set of such clones may be processed in parallel for e.g. subtractive comparisons between cDNA populations. For example, library to library comparisons may be made between for instance a library of all genes expressed in a given tissue and on the other hand all sequences located in a particular region of the genome, from yeast artificial chromosomes, subcloned in a circular single stranded plasmid library. This is, for example, useful when a disease gene has been located to a region by linkage analysis and it is known to be expressed in a particular tissue.

The necessary vector may be prepared by ligating oligonucleotides to a restriction digested plasmid to generate, on one hand, a recognition motif for an asymmetrically cleaving enzyme, such as GsuI, and, on the other hand, a nearby situated rare restriction site, such as NotI. One way of constructing the vector is by inserting two oligonucleotide dimers to two different ends, generated by digestion with two restriction enzymes.

Recombinant molecules are then produced by ligating blunt end DNA fragments, e.g. generated by AluI digestion, to the vector. The constructs obtained are transformed into bacteria and single-stranded recombinant molecules are generated.

Figure 2:
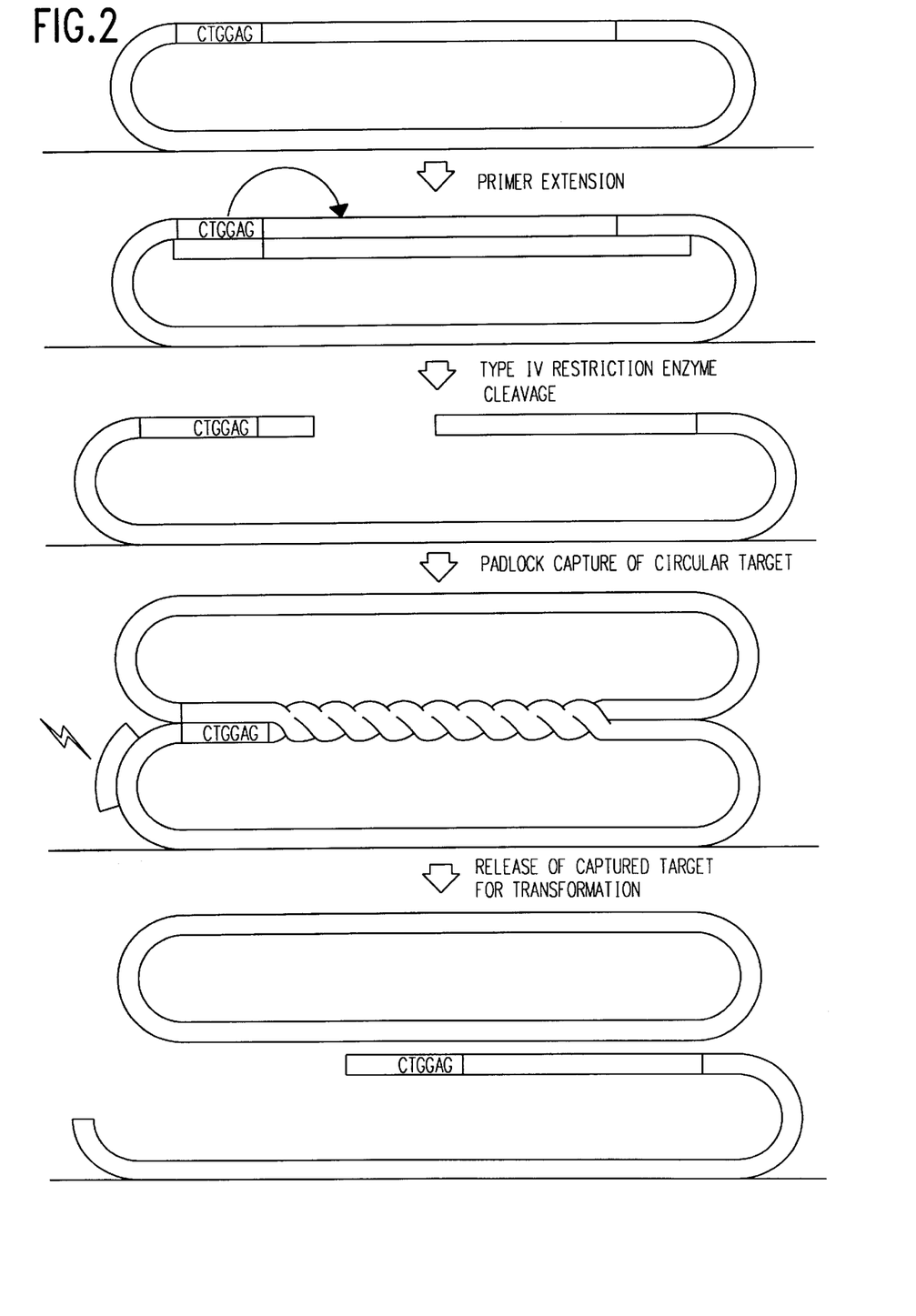
FIG. 2 is a schematic representation of an immobilized vector containing a GsuI site, the cleavage thereof to prepare a circularizable probe, and the use of the latter for the capture and subsequent release of single-stranded circular target molecules.

These circular single-stranded molecules are then immobilized in patches on a solid phase, e.g. a membrane, as schematically illustrated in FIG. 2. A primer is hybridized to the vector molecule and extended using a DNA polymerase, rendering the recognition sequence for the asymmetrically cleaving enzyme double stranded and permitting cleavage of the insert. After digestion of the molecules with the enzyme, the fragments of extended molecules are removed by denaturing washes.

The immobilized circularizable probes obtained may be used for trapping target molecules, as is also illustrated in FIG. 2. To this end, a population of recombinant clones prepared as above is turned into single-stranded circular molecules. For comparisons between directionally cloned cDNA populations, this library, should, of course, be of the opposite polarity to the above construct. Further, the vector must not have the same rare-cutter enzyme site or at least not the same polarity of the sequence surrounding the recognition sequence. These molecules are now exposed to the immobilized probes and trapped by ligation, followed by stringent washes.

An oligonucleotide is then annealed to the region of the rare-cutter side on the capture vectors, and these are linearized by digestion with the rare cutter enzyme. Trapped clones are released by denaturing washes, repaired, and transformed into bacteria for molecular cloning.

Since the above described approach is based on an intramolecular reaction (ligation), large numbers of clones may be treated and then applied as capture probes in the same reaction. In contrast, e.g. PCR will only permit a handful of reactions to be performed in the same reaction due to the problem of nonspecific crosstalk between primers.

In the following, the invention will be illustrated by a non-limiting example.

EXAMPLE

Chemical Oligonucleotide Synthesis

The following oligodeoxynucleotides were synthesized on an Applied Biosystems 394 DNA/RNA synthesizer (Applied Biosystems Inc., USA):

Omni1: 5' AATTG ACCGT TAGCA AACTGG AG 3'

Omni2: 5' CTCCA GTTGC TAACG GTC 3'

BOmni1: Omni1 above syntesized with the addition of a 5' biotin residue.

(In the sequences for Omni1 and Omni2 the recognition sequence for the restriction enzyme GsuI has been underlined.)

Control primer A1: 5' AATTG ACCGT TAGCA ACTGG AGCTC AGCAG CCCGT GAT 3'

Control primer AM1: 5' CTC AGCAG CCCGT GAT 3'

Control primer A2: 5' AATTG ACCGT TAGCA ACTGG AGCTT CCAGA GTCAG ATC 3'

Control primer AM2: 5' CTTCC AGAGT CAGAT C 3'.

Construction of the Cloning Vector pRIMER

Plasmid pBLUESCRIPT M13 was digested with EcoRI and, in the same reaction, the oligonucleotide duplex Omni1 and Omni2 were ligated to the restriction fragment ends (FIG. 1A, part A). 20 U of EcoRI were added to 5 µg of the plasmid in a final volume of 10 µl containing 10 mM Tris-HCl, pH 7.5, 10 mM MgCl$_2$, 50 mM potassium acetate, and 5 mM ATP. After 3 hours at 37° C., 2.5 U of T4 DNA ligase were added with oligonucleotides Omni1 and Omni2 at 25 µM each. The reaction was left at 14° C. over-night. Linearized vector molecules with added linkers were gel purified in a 1.5% NuSieve GTG agarose gel (Nalgene), and used as a cloning vector.

Cloning of Alu-digested Fragments and Screening for Positive Clones

AluI-digested fragments from the human ameliogenin gene located on the X chromosome were ligated into the above vector and introduced in strain DH5 of E. coli (FIG. 1A, part B). Individual bacterial clones were transferred with-a toothpick from the agar plate to 100 µl of water in an Eppendorf tube, the samples were boiled for 5 minutes, and then chilled on ice. Cell debris was pelleted in a short centrifugation and one µl of the supernatant was used as a source of template in a 30 µl PCR with the single primer BOmni1 at 1 µM. 10 µl aliquots of the PCR samples were separated in a 1.5% agarose gel to quantitate and determine the size of the amplification products before the inserts were used for synthesis of amplification primers.

Enzymatic Synthesis of Specific Amplification Primers

In order to prepare amplification primers (FIG. 1A, part C), 2 µg of inserts that had been amplified with BOmni1 were gel purified in 2% NuSieve GTG agarose (Nalgen) and digested with 8 units of GsuI (Fermentas, Vilnius, Lithuania) in 15 µl of 100 mM NaCl, 50 mM Tris-HCl, pH 7.9, 10 mM MgCl$_2$, 1 mM dithiothreitol, and BSA at 0.1 µg/µl for 3 hours at 37° C.

The digestion products were separated by electrophoresis in a 2% agarose gel. End fragments released from the amplification products by enzymatic digestion were isolated from the gel, taking care not to contaminate the material with undigested material.

Isolated fragments were treated with λ exonuclease (Life Technologies) destroying DNA strands with 5'-phosphate groups but sparing strands with a biotin residue at the 5'-position. The reactions were performed in a final volume of 10 µl, containing approximately 200 ng of end fragments, 50 ng/µl BSA, 2 units of λ exonuclease, 67 mM glycine-KOH, pH 9.4, 2.5 mM MgCl$_2$ for 1 hour at 37° C. The DNA was preheated for 5 minutes at 94° C. before the reaction. Remaining 5'-biotinylated DNA strands were used as amplification primers.

Amplification Using Enzyme-synthesized Primers

Enzymatically synthesized primers were used at a concentration of 0.05 µM, together with oligonucleotide Omni1 at 1 µM, for amplification of human genomic DNA samples (FIG. 1B, part D). During the first 5 amplification cycles, annealing times were set at 10 minutes followed by a regular amplification protocol. Since the melting temperatures are not known for the template-specific 3'-ends of the amplification primers, two different different amplification programs were tried for each primer pair. The complete amplification program was as follows: 5 cycles of 94° C. for 1 minute, annealing at 40° C. or 55° C. for 5–15 minutes, and 72° C. for 1 minute, followed by 30 cycles of 94° C. for 1 minute, 55° C. for 1 minute, and 72° C. for 1 minute.

Figure 3:
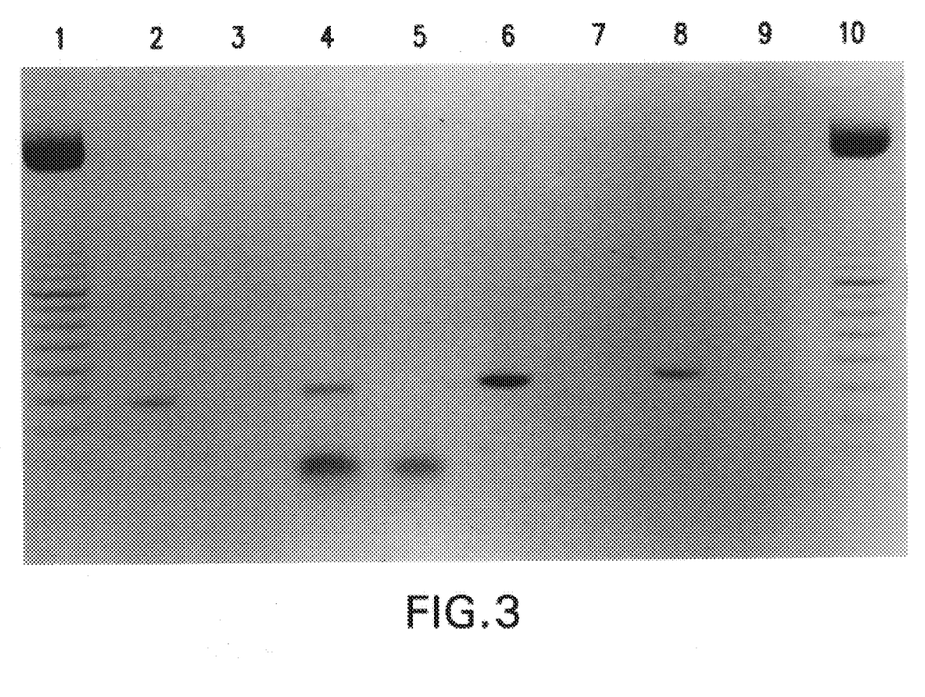
FIG. 3 is a photograph of an autoradiograph of a comparison of amplification products obtained by PCR using sets of primers derived by solid-phase chemical synthesis or enzymatically. For an AluI fragment of a known DNA sequence, specific 16-mer primers that were synthesized by standard solid phase chemistry, were compared with similarly constructed 38-mer primers of the same 16-base sequence at the 3'-end, and with an enzymatically synthesized primer pair, expected to have the same 38-mer sequence as the chemically synthesized oligonucleotides of this size.

The autoradiograph in FIG. 3 illustrates agarose gel electrophoresis of the results of amplification reactions using either chemically synthesized, 16 bases long primers (Am1 and Am2), lane 2 and lane 3 (without template); the same 16 bases with additionally 22 bases at the 5' ends identical to Omni1 (A1 and A2), lane 4 and lane 5 (without template); amplification with BOmni1 from the plasmid clone used to generate the primers, lane 6 and lane 7 (without template); or enzyme-synthesized primers for a 200 bases long AluI fragment of known DNA sequence, assumed to be identical in sequence to oligonucleotides A1 and A2, lane 8 and lane 9 (without template). Lanes 1 and 10 are 100 bp ladders. As appears from the autoradiograph, all three pairs of oligonucleotides, when applied to human genomic DNA samples, gave rise to amplification products of approximately the same size. This is the size expected for these primers. In the absence of added template DNA, no amplification products were observed, affirming that the amplification products did not represent copies of contaminating undigested amplified clone inserts.

Identification of Polymorohic Sequences

The amplification primer Omni1 was kinased with $^{32}$P in a 30-minute reaction at 37° C. in 50 mM Tris-HCl, pH 7.5, 50 mM KCl, 10 mm MgCl$_2$, and 0.5 ICI γ$^{32}$P ATP. The primer was used for amplification of genomic DNA samples, followed by separation of the products by 6% polyacrylamide denaturing gel electrophoresis. Size variation among amplification products was revealed by autoradiography.

We claim:

1. A method of making amplification primers, said method comprising:
   (a) ligating a DNA sequence into a linear nucleotide sequence to form a nucleic acid sequence comprising said DNA segment and an asymmetrically cleaving restriction enzyme recognition sequence at each end of said DNA segment;
   (b) amplifying said nucleic acid sequence, using a primer having a sequence corresponding to said recognition sequence, to form an amplification product;
   (c) forming restriction fragments by digesting said amplification product with said asymmetrically cleaving restriction enzyme, each of said restriction fragments having two ends, wherein two of said restriction fragments contain said asymmetrically cleaving restriction enzyme recognition sequence at one of said two ends;
   (d) purifying said restriction fragments containing said asymmetrically cleaving restriction enzyme recognition sequence at one of said two ends; and
   (e) rendering said restriction fragments of step (d) single-stranded to form said amplification primers.

2. The method of claim 1, wherein said linear nucleotide sequence is a cleaved vector.

3. The method of claim 1, wherein the 5' end of each of said primers is protected from exonuclease digestion, and
   wherein step (e) comprises digesting said restriction fragments with λ exonuclease.

4. The method of claim 3, wherein the 5' end of each of said primers is protected from exonuclease digestion by biotinylation.

5. The method of claim 1, wherein in said step (a), the same recognition sequence is formed at each end of said DNA segment, and wherein in said step (c), the restriction fragments are formed using one asymmetrically cleaving restriction enzyme.

6. The method of claim 1, wherein said step (b) further comprises
   (b1) immobilizing said amplification product on a solid support.

7. The method of claim 1, wherein said asymmetrically cleaving restriction enzyme is a type III restriction enzyme.

8. The method of claim 1, wherein said asymmetrically cleaving restriction enzyme is a type IV restriction enzyme.

9. The method of claim 8, wherein said type IV restriction enzyme is GsuI.

10. The method of claim 8, wherein said type IV restriction enzyme is Eco57I.

11. The method of claim 8 wherein said type IV restriction enzyme is MmeI.

12. The method of claim 1 wherein said asymmetrically cleaving restriction enzyme is Eco15.

13. The method of claim 1 wherein said asymmetrically cleaving restriction enzyme is HinP15I.

14. A method of amplifying a fragment of DNA, said method comprising
   (a) making amplification primers according to the method of any one of claims 1–3; and
   (b) amplifying said fragment of DNA using said amplification primers.

15. The method of claim 14, said method further comprising
   (c) further amplifying said fragment of DNA using linker primers.

16. The method of claim 14, wherein said fragment of DNA is genomic DNA.

17. A method of making a circularizable DNA probe, said method comprising
   (a) ligating a DNA fragment into a vector to form a DNA sequence comprising said DNA fragment and a recognition sequence for an asymmetrically cleaving restriction enzyme at one end of said fragment;
   (b) transforming bacteria with said DNA sequence;
   (c) generating a single-stranded molecule comprising said DNA fragment and a recognition sequence for an asymmetrically cleaving restriction enzyme at one end of said DNA fragment;
   (d) immobilizing said singe-stranded molecule on a solid phase;
   (e) hybridizing to said single-strained molecule a primer corresponding to said asymmetrically cleaving restriction enzyme recognition sequence;
   (f) forming a double-stranded recognition sequence by extending said primer; and
   (g) digesting said double-stranded recognition sequence with said asymmetrically cleaving restriction enzyme to form a circularizable DNA probe.

18. The method of claim 17, wherein said recognition sequence is present in said vector prior to the ligation of said DNA fragment into said vector.

19. The method of claim 17, wherein said recognition sequence is formed when said DNA fragment is ligated into said vector.

20. The method of claim 17, wherein said asymmetrically cleaving restriction enzyme is a type III restriction enzyme.

21. The method of claim 17, wherein said asymmetrically cleaving restriction enzyme is a type IV restriction enzyme.

22. The method of claim 21, wherein said type IV restriction enzyme is GsuI.

23. The method of claim 21, wherein said type IV restriction enzyme is Eco57I.

24. The method of claim 21, wherein said type IV restriction enzyme is MmeI.

25. The method of claim 17, wherein said asymmetrically cleaving restriction enzyme is Eco15.

26. The method of claim 17, wherein said asymmetrically cleaving restriction enzyme is HinP15I.

27. A method of capturing a target nucleic acid molecule, said method comprising
  (a) making a circularizable DNA probe according to the method of claim 17, wherein said circularizable DNA probe hybridizes to said target nucleic acid molecule;
  (b) hybridizing said target nucleic acid molecule to said circularizable DNA probe; and
  (c) forming a circular molecule by joining the ends of said circularizable DNA probe using a ligase to catenate said circularizable DNA probe to said target nucleic acid molecule.

28. The method of claim 27, further comprising
  (d) cleaving said circular molecule to release said target nucleic acid molecule.

29. A kit for making amplification primers, said kit comprising
  (i) a vector containing a cleavage site for the insertion of a DNA fragment, and said vector also containing a recognition sequence for an asymmetrically cleaving restriction enzyme on each side of said cleavage site;
  (ii) a primer which hybridizes to said vector; and
  (iii) an asymmetrically cleaving restriction enzyme that recognizes said recognition sequence to cleave within the inserted DNA fragment.

30. A kit for making a circularizable probe, said kit comprising
  (i) a single-stranded vector containing a cleavage site for the insertion of a DNA fragment, a single recognition sequence for an asymmetrically cleaving restriction enzyme on one side of said cleavage site, and a single recognition sequence for a further restriction enzyme, wherein said further restriction enzyme is different than said asymmetrically cleaving restriction enzyme; and
  (ii) a primer which hybridizes to said vector at said single recognition sequence for said further restriction enzyme that is different than said asymmetrically cleaving restriction enzyme.

* * * * *

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (ii) MOLECULE TYPE: DNA (synthetic)

(xi) SEQUENCE DESCRIPTION: SEQ ID NO: 1:

AATTGACCGT TAGCAACTGG AG                                                    22

(2) INFORMATION FOR SEQ ID NO: 2:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: DNA (synthetic)

(xi) SEQUENCE DESCRIPTION: SEQ ID NO: 2:

CTCCAGTTGC TAACGGTC                                                         18

(2) INFORMATION FOR SEQ ID NO: 3:

(i) SEQUENCE CHARACTERISTICS:
       (A) LENGTH: 38 base pairs
       (B) TYPE: nucleic acid
       (C) STRANDEDNESS: single
       (D) TOPOLOGY: linear (ii) MOLECULE TYPE: DNA (synthetic)

(xi) SEQUENCE DESCRIPTION: SEQ ID NO: 3:

AATTGACCGT TAGCAACTGG AGCTCAGCAG CCCGTGAT                                   38

(2) INFORMATION FOR SEQ ID NO: 4:

(i) SEQUENCE CHARACTERISTICS:
       (A) LENGTH: 16 base pairs
       (B) TYPE: nucleic acid
       (C) STRANDEDNESS: single
       (D) TOPOLOGY: linear (ii) MOLECULE TYPE: DNA (synthetic)

(xi) SEQUENCE DESCRIPTION: SEQ ID NO: 4:

CTCAGCAGCC CGTGAT                                                           16

(2) INFORMATION FOR SEQ ID NO: 5:

(i) SEQUENCE CHARACTERISTICS:
       (A) LENGTH: 38 base pairs
       (B) TYPE: nucleic acid
       (C) STRANDEDNESS: single
       (D) TOPOLOGY: linear (ii) MOLECULE TYPE: DNA (synthetic)

(xi) SEQUENCE DESCRIPTION: SEQ ID NO:5:

-continued

```
AATTGACCGT TAGCAACTGG AGCTTCCAGA GTCAGATC                            38
```

(2) INFORMATION FOR SEQ ID NO: 6:

(i) SEQUENCE CHARACTERISTICS:
        (A) LENGTH: 16 base pairs
        (B) TYPE: nucleic acid
        (C) STRANDEDNESS: single
        (D) TOPOLOGY: linear     (ii) MOLECULE TYPE: DNA (synthetic)

(xi) SEQUENCE DESCRIPTION: SEQ ID NO: 6:

```
CTTCCAGAGT CAGATC                                                    16
```